United States Patent
Urbaszek et al.

(10) Patent No.: US 7,859,400 B2
(45) Date of Patent: Dec. 28, 2010

(54) METHOD AND APPARATUS FOR AUTOMATIC REGISTRATION OF A PATIENT-BOUND MEDICAL UNIT

(75) Inventors: Albrecht Urbaszek, Hausen (DE); Sven Bode, Berlin (DE); Michael Diebold, Berlin (DE); Andre Seidelt, Berlin (DE)

(73) Assignee: Biotronik CRM Patent AG, Baar (CH)

( * ) Notice: Subject to any disclaimer, the term of this patent is extended or adjusted under 35 U.S.C. 154(b) by 882 days.

(21) Appl. No.: 11/754,976

(22) Filed: May 29, 2007

(65) Prior Publication Data

US 2007/0282175 A1    Dec. 6, 2007

(30) Foreign Application Priority Data

May 30, 2006    (DE) .................. 10 2006 024 988

(51) Int. Cl.
*G08B 1/08* (2006.01)
(52) U.S. Cl. ............ 340/539.12; 340/505; 340/538.15; 340/539.1; 340/539.11; 340/539.13; 340/539.23; 340/10.1; 340/286.08; 340/573.1
(58) Field of Classification Search ........... 340/505, 340/538.15, 539.1, 539.11, 539.12, 539.13, 340/539.21, 539.23, 573.4, 10.1, 286.08, 340/573.1
See application file for complete search history.

(56) References Cited

U.S. PATENT DOCUMENTS 6,878,112 B2    4/2005    Linberg et al.

2003/0025604 A1*    2/2003    Freeman .................. 340/573.1
2005/0149283 A1    7/2005    Herrmann et al.

FOREIGN PATENT DOCUMENTS

| DE | 10340064 | 4/2005 |
|---|---|---|
| EP | 1081895 | 3/2001 |
| FR | 2800481 | 5/2001 |
| WO | WO 01/47411 | 7/2001 |
| WO | WO 02/051500 | 7/2002 |
| WO | WO 03/095024 | 11/2003 |

OTHER PUBLICATIONS

Jones KL, Manwaring ML, Manwaring KH, "A Protocol for Automatic Sensor Detection . . ." Proceedings of Eleventh IEEE Symposium on Computer-Based Medical Systems, 1998, p. 311-316.
German Search Report, dated Apr. 11, 2007.
European Search Report, dated May 21, 2008.

* cited by examiner

*Primary Examiner*—Daryl Pope
(74) *Attorney, Agent, or Firm*—ARC IP Law, PC; Joesph J. Mayo

(57) ABSTRACT

A method for automatic registration of a patient-bound medical device with a remote data processing system, physician identification data being transmitted to the patient-bound medical device, the physician identification data being combined together with device identification data to form a registration message, the registration message being transmitted from the patient-bound medical device to the data processing system, and the data processing system checking the data contained in the registration message and, in case of success, performing the registration, as well as apparatuses for this purpose.

23 Claims, 2 Drawing Sheets ized identification of the patient-bound medical device. In this way, a check performed by the data processing and monitoring system is not limited to the identity of the patient-bound medical device, but may also include user- and patient-specific components by a simple expansion of the data structure without changes of the infrastructure being necessary.

METHOD AND APPARATUS FOR AUTOMATIC REGISTRATION OF A PATIENT-BOUND MEDICAL UNIT

This application takes priority from German Patent Application DE 10 2006 024 988.7 filed 30 May 2006, the specification of which is hereby incorporated herein by reference.

BACKGROUND OF THE INVENTION

1. Field of the Invention

Embodiments of the invention relate to a method for automatic registration of a patient-bound medical device with a remote data processing system, as well as a programming device for this purpose as claimed herein.

2. Description of the Related Art

Configurations are used for the continuous monitoring of vital functions of the human body in which a patient-bound medical device performs the measurement of the bodily signals, executes a partial initial processing of the signals, and then transmits this data to a remote data processing and monitoring center. Such a system is described in Published Application WO 03/095024 A2.

Furthermore, it is suggested therein that the patient-bound medical device be equipped with means to retrieve the confirmation of previously stored individuals electronically before the transmission of concrete patient measured data, and check whether a monetary electronic credit balance also stored in the device is sufficient to cover the measured data monitoring service.

For the initial registration of a patient-bound medical device which has just been put into operation with the patient, it is necessary according to the prior art to transmit device identification data, such as the serial number of the patient-bound device, from the physician in the hospital to a user at the central monitoring system by fax or in another way and then input the device identification data of the patient-bound medical device manually into an input form of the monitoring system, to ensure an identification of the system components and/or access authorization on the monitoring system side or on both sides in this way.

Due to this transmission in registration according to the prior art, which is subject to media breakdown and requires a manual input, the disadvantage arises that a disadvantageous time delay arises between the initialization of the patient-bound medical device and its practical readiness for use after completion of the registration procedure, which is caused by the administration effort. The device identification data may additionally be corrupted or lost during the transmission, which requires additional effort for correcting these errors.

In addition, the effort required for inputting the data reduces the acceptance of known devices on the part of the physicians.

BRIEF SUMMARY OF THE INVENTION

It is accordingly the object of the present invention to specify a method and apparatus which allow automatic registration of a patient-bound medical device with a central data monitoring station and avoid the disadvantages cited in the prior art.

This object is achieved according to embodiments of the invention by the subject matter as claimed herein.

The achievement of the object according to the claims is represented by a method for automatic registration of a patient-bound medical device with a remote data processing system:

physician identification data being transmitted to the patient-bound medical device, the physician identification data being combined with device identification data in a registration message, the registration message being transmitted from the patient-bound medical device to the data processing system, and the data processing system checking the data contained in the registration message and, if successful, performing the registration.

It has the Following Advantages:

Because the physician identification data is transmitted combined in a registration message together with device identification data by the patient-bound medical device to the data processing system, the data set necessary for the registration procedure with the central data processing/monitoring station is provided secure from manipulation in a way which incorporates rapid and existing infrastructure apparatus and without interposing activity by a human operator which is possibly subject to error. It is possible in this way to automatically check the identity of the patient-bound medical device by the central data processing/monitoring station during all logging in and logging out procedures subsequent to the registration procedure.

Because the physician identification and device identification data is combined in closed form in the registration message, the unique assignment of the identification data to one another is ensured. In addition, the data is brought into a form of a data container in this way which is recognized immediately by the data processing system as a registration message and triggers the registration of the patient-bound medical device in the data processing system after it has been electronically transmitted.

Because the procedure of checking the data contained in the received registration message occurs in the data processing system as a central monitoring station, if necessary, parameter data important for the performing the check may be changed quickly in the system and keeping this data, which is relevant for deciding the registration, consistent is made significantly easier by the central storage of all relevant validation and authentication information. Furthermore, due to the improved possibilities of shielding of the central system, undesired manipulation access to the validation and authentication data may be avoided with less technical effort.

The achievement of the object according to embodiments of the invention according to the claims is represented by a programming device for programming a patient-bound medical device having at least one interface for transmitting and receiving data and having a memory for storing and retrieving data, means for inputting user data, and means for querying device identification data from the patient-bound medical device, characterized in that the programming device is implemented to generate a data structure from the device identification data and the user data and is also implemented to serialize and transmit the data structure as the registration message to the patient-bound medical device.

Because the programming device according to the claims is implemented to generate a data structure made of the device identification data and the user data, it is possible to perform the data processing step of assembling the registration-relevant data in the system component of programming device, which typically, in contrast to the system component of the patient-bound medical device, may be supplied more easily with storage, processor, and power resources. Furthermore, in this way user data, with the addition of personal physician or patient data, may be combined with the device identification data at this point and the registration message produced in the programming device may be transmitted to the patient-bound medical device to be relayed to the remote data processing system. Both in this context and also in the entire remaining scope of the subject matter suggested in this application, the implementation of apparatus features may be performed as desired by more or less specific hardware and hardware configurations and also by programming apparatus and their interactions.

The achievement of the object according to the claims is represented by a programming device for programming a patient-bound medical device having at least one interface for transmitting and receiving data and having a memory for storing and retrieving data, means for inputting user data and means for querying device identification data from the patient-bound medical device, characterized in that the programming device is implemented to generate a data structure from the device identification data and the user data, is implemented to serialize and transmit the data structure as a registration request to a data processing system, and is also implemented to generate and transmit a triggering command for a registration message to a patient-bound medical device.

Because the programming device according to the claims is implemented to transmit a triggering command for a registration message to a patient-bound medical device and, in addition, to transmit user data which may contain personal physician or patient data in clear text together with device identification data directly to the remote data processing system at the central monitoring station, it is made possible to transmit a first data packet, which is light in data, as the registration message on a first communication pathway and a second data packet comprising a larger quantity of data as a registration request on a second data pathway.

In this way, advantageously, firstly the reliability of the automated registration is increased and secondly the quantity of the data to be transmitted is tailored to the capacity of the particular data channel transmitting the data.

Both inventions according to the claims share the advantage that a data container tailored to the capacity and the special requirements on reliability and data security of the particular communication channel (registration message, registration request) is generated and filled with data and the data container is thus automatically recognizable and its content is automatically processable.

The achievement of the object according to embodiments of the invention according to the claims is represented by a patient-bound medical device having at least one communication interface and stored device identification data, characterized in that it is implemented for transmitting a registration message to a data processing system. Typical components of a patient-bound device of this type are an implant, such as a cardiac pacemaker or defibrillator, and a patient device, which is worn by a patient and wirelessly communicates with the implant. The implant also operates basically independently of the patient device. However, the present invention is precisely concerned with the interaction of patient device and implant, so that both devices together are referred to as the patient-bound device.

Because the device is implemented to transmit a registration message to a data processing system, this achievement of the object has the advantageous effect that the patient-bound medical device, in addition to its intrinsic function of measuring and transmitting measured data, is thus also set up to transmit a registration message, which is uniquely recognizable as such, having the data relevant for the registration, to a data processing system, which recognizes the registration message as such and performs the processing of the data contained in the registration message.

The achievement of the object according to embodiments of the invention according to the claims is represented by a data processing system having at least one communication interface for receiving and transmitting messages and a memory for storing and retrieving data, characterized in that it is implemented to receive a registration message from a patient-bound medical device, to check the data contained therein, and to register and to transmit a confirmation message or an error message to a patient-bound medical device.

The data processing system thus implemented therefore has the advantage that, using system and communication apparatus situated in the data processing system, it may receive and recognize a registration message from a patient-bound device and may check whether the data has been correctly and completely received and whether the registration is permissible as a whole, it may possibly use the data contained in the registration message for the registration and in any case it may transmit back a message about the success of the automatic registration to the patient-bound medical device and the programming device.

The achievement of the object according to embodiments of the invention according to the claims is represented by a configuration for executing the method for automatic registration of a patient-bound medical device at a remote data processing system according to the claims having a programming device according to the claims, a patient-bound medical device according to the claims, and a data processing system according to the claims.

Advantageous refinements of embodiments of the invention according to the claims are possible according to the particular subclaims referring back thereto and are briefly explained in the following:

The method according to the claims may advantageously be refined in that the device identification data is assembled from identification data of individual system components of the patient-bound medical device. In this way, it is made possible in the course of the automatic registration to uniquely identify the individual system components from which the patient-bound medical device may be assembled, such as implant on one hand and patient device on the other hand, and to perform a compatibility check of the system components, for example.

Such a compatibility check is possible according to an advantageous refinement of the method and may be performed by the data processing system. A further advantageous embodiment feature provides monitoring the authorization of the registration procedure on the basis of the physician identification data contained in the registration message during the check of the data contained in the registration message by the data processing system as the central monitoring device.

According to an embodiment variation of the method, the device identification data is first queried by a programming device from the patient-bound medical device and combined with physician identification data stored in the programming device to form the registration message and transmitted by the programming device to the patient-bound medical device. In this way, it is not only possible to transmit the registration message via the intrinsic system communication pathways, but rather the preparation procedures of the registration message are also performed in the programming device, which may typically be provided with more powerful system resources, and which typically contains a better user interface than a patient-bound medical device. In an advantageous embodiment of this variation, further personal data, about physician and patient, for example, or further administration data may be incorporated in the physician identification data. Furthermore, in an advantageous embodiment, the data processing system transmits a confirmation in case of successful registration and an error message in case of failed registration to the patient-bound medical device, by which the intrinsic system communication resources may also be used here bidirectionally for the acknowledgment about the registration process.

In a further embodiment variation of the method, physician identification data is transmitted from the programming device to the patient-bound medical device, for which a key expression is advantageously used. In this way, the volume of the data to be transmitted by the patient-bound medical device and the storage space required in the patient-bound medical device are reduced. This advantage especially appears if the method is implemented in such a way that a command for triggering a registration message is transmitted by the programming device to the patient-bound medical device and the physician identification data is combined in the patient-bound medical device with the device identification data stored in the patient-bound medical device to form the registration message. In this way, a data packet which is light in data is generated where the system-critical device identification data is already permanently stored. In this way, transmission errors are reduced and manual inputs or transmissions of device identification data are avoided.

In an advantageous embodiment of this variation, a registration request is transmitted from the programming device to the data processing system. In this way, via a second communication pathway independent of the patient-bound medical device (e.g., Internet), a parallel registration request provided with additional data may be transmitted, in which device identification data and/or physician identification data and/or personal data may advantageously be incorporated. The method may advantageously be refined in that the data processing system transmits a confirmation directly to the programming device in case of successful registration and otherwise transmits an error message.

If the method is advantageously refined so that the data contained in the registration message is compared to the data contained in the registration request in the data processing system, during the automatic recognition and processing of the registration message in the registration request, the validity of the included data and/or the reliability of the registration is not only established by a comparison to the data centrally stored in the data processing system, but rather the consistency of the data is also ensured by bringing together registration message and request. During the check in the data processing system, it is advantageous in the scope of an advantageous refinement of the method to check whether precisely one registration message has been received for a received registration request (or, vice versa, precisely one received registration request for a received registration message). For the advantageous selection of communication channels in the scope of the method, firstly an infrared connection may be produced between the programming device and the patient-bound medical device (advantageously in the form of a serial IR interface), secondly an Internet connection may be produced between the programming device and the data processing system, and thirdly a mobile wireless connection may be produced between the patient-bound medical device and the data processing system.

To establish the identity and the compatibility of individual system components of the patient-bound medical device, it is advantageous to refine the programming device in such a way that the data structure assembled therein has a first data field for storing the device identification data of a first system component of the patient-bound medical device as well as a second data field for storing the device identification data of a second system component of the patient-bound medical device and further data fields for storing user data, which may include personal data about physician and/or patient, as well as identification data, which is used for the identification as a registration message.

If the patient-bound medical device is advantageously refined in such a way that it is implemented to receive and process physician identification data, and to receive and process a triggering command for a registration message from the programming device, it is possible to receive physician identification data and separately a command for preparing a registration message directly independently. On the basis of the triggering command for a registration message, according to one embodiment of the patient-bound medical device, a data structure is generated from the device identification data and the previously transmitted physician identification data, which may preferably be an alphanumeric character chain, by a corresponding programming apparatus. Furthermore, according to the advantageous refinement, programming means are contained which are implemented to serialize this data structure, identify it as a registration message, and transmit it to the data processing system.

The refinements of the data processing system according to embodiments of the invention may be inferred from the claims referring back to the claims and the method and apparatus refinements explained above have corresponding advantageous apparatus.

BRIEF DESCRIPTION OF THE FIGURES

The present invention is explained on the basis of two figures using exemplary embodiments.

DETAILED DESCRIPTION OF THE INVENTION

Figure 1:
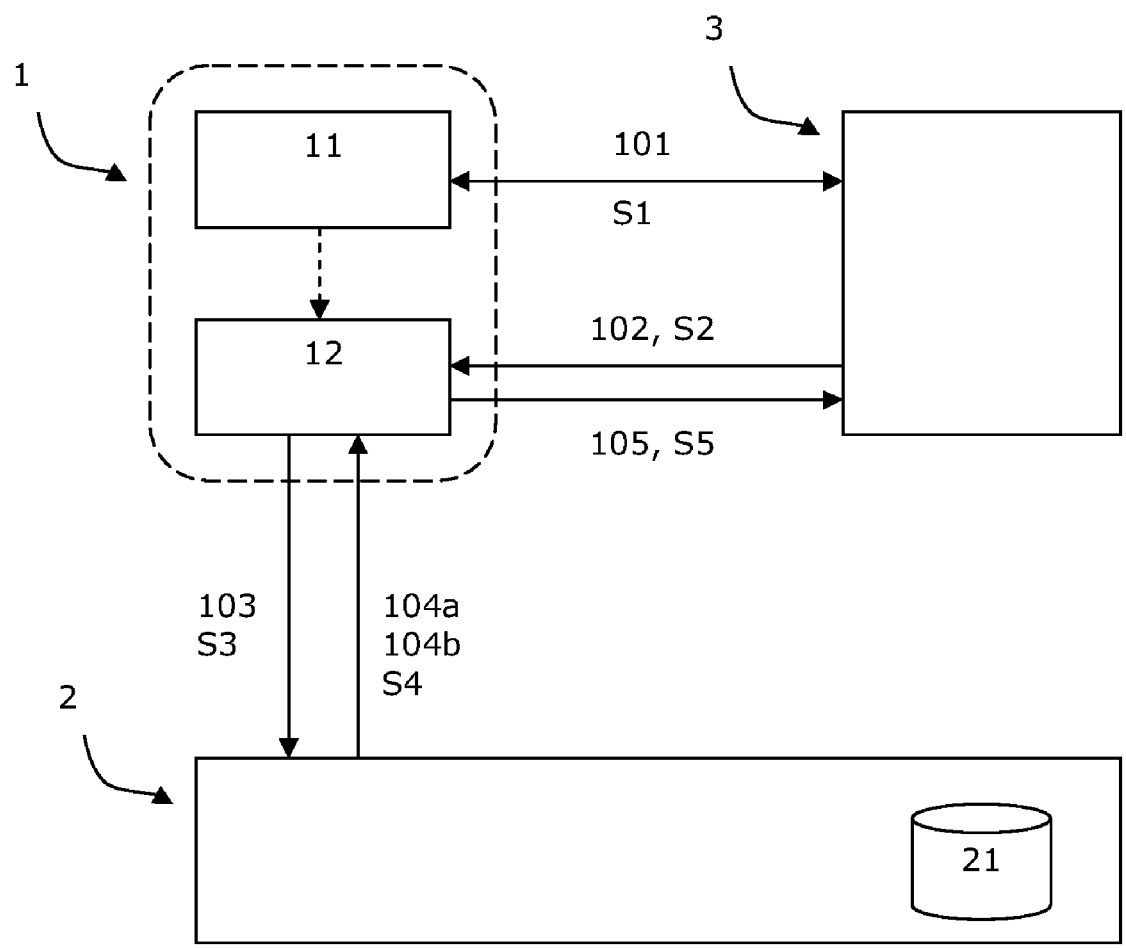
FIG. 1 shows system components and communication procedures during the automatic registration according to a first embodiment variation.

FIG. 1 shows a schematic overview of an overall system for telemedical patient monitoring having the system components of patient-bound medical device 1, data processing system as central monitoring station 2, and programming device 3. The patient-bound medical device 1 is continuously located in direct proximity to the patient to be monitored and in the present case comprises two system components, implant 11 and patient device 12, which are connected via a wireless communication interface, which may be designed as unidirectional from the implant to the patient device or bidirectional. For the initialization and/or programming, the programming device 3 is typically brought into spatial proximity to the patient-bound device 1. The data processing system 2 is situated significantly distant from these above-mentioned components as the central monitoring device, typically for multiple patient-bound devices 1.

In this example, the communication between patient-bound device 1, more precisely: between patient device 12, and data processing system 2 therefore occurs via a mobile wireless connection, while the communication between patient-bound device 1 and programming device 3 occurs via an infrared interface between patient device 12 and programming device 3 and/or a further wireless local connection between implant 11 and programming device 3.

The data processing system 2 has a databank 21, in which manifold different data is stored, such as technical data on types and individual examples of patient-bound medical devices, personal data about physician and patient, the monitored measured data of the vital functions of the patient, or software components for remote maintenance of the patient-bound medical device.

In the scope of this entire patent application and all exemplary embodiments, "personal data" typically identifies alphanumeric character chains situated in multiple fields.

Before, in running operation, the patient-bound medical device 1 transmits measured data via patient device 12 at periodic intervals to the remote data processing system 2 via a mobile wireless connection, as soon as possible after implant 11 and patient device 12 are first put into operation, registration of the patient-bound medical device 1 with central system 2 must occur.

For this purpose, firstly the implant is queried in the bidirectional communication procedure S1 by the programming device 3. In the present case, this is implemented by a local wireless connection, alternatively, however, communication with the patient device 12 via infrared interface is also conceivable, which accordingly relays the information request via a local wireless connection to the implant 11 and correspondingly transmits the queried information received from the implant 11 via the infrared interface to the programming device 3.

After query of the implant 11 (in this case directly via a separate local wireless connection) an infrared connection is produced between the programming device 3 and the patient device 12 in a way not shown in greater detail here. The user data, which, in addition to the personal data of the attending physician also comprises further data about the patient and further useful data, is checked by the physician in the programming device 3 and is confirmed by specification of his user identification, the physician having to authenticate himself by specifying user group, name, and password.

The device identification data 101 queried from the implant 11 in step S1 is then combined in programming device 3 with the user data which contains the cited physician identification data and the remaining data, to form a data structure 102 identified as a registration message, which is transmitted serialized to the patient device 12 in the communication step S2 to be relayed to the remote data processing system 2. The relay of the registration message 102 assembled in the programming device 3 by the patient device 12 is performed in step S3 via a mobile wireless connection (GPRS). The data processing system 2 processes the received registration message 103 by reading out the device identification data, comprising the serial number of the implant 11 and the serial number of the patient device 12, and the physician identification data and further user data and checking whether the user is authorized to register the patient-bound device 1 and whether implant and patient device are compatible with one another. For this purpose, the data processing 2 accesses data stored in data bank 21. If the result of the automated check, in which further technical and administrative information and boundary conditions may be incorporated, is positive, a success message 104*a* (in case of a negative check result, an error message 104*b*) is transmitted in communication step S4, which is received by the patient device 12 and relayed via infrared interface in communication step S5 to programming device 3. The programming device 3 outputs a corresponding confirmation or error message on the display screen.

The deregistration, i.e., the final logging out from the running measured data monitoring, may be performed analogously.

Figure 2:
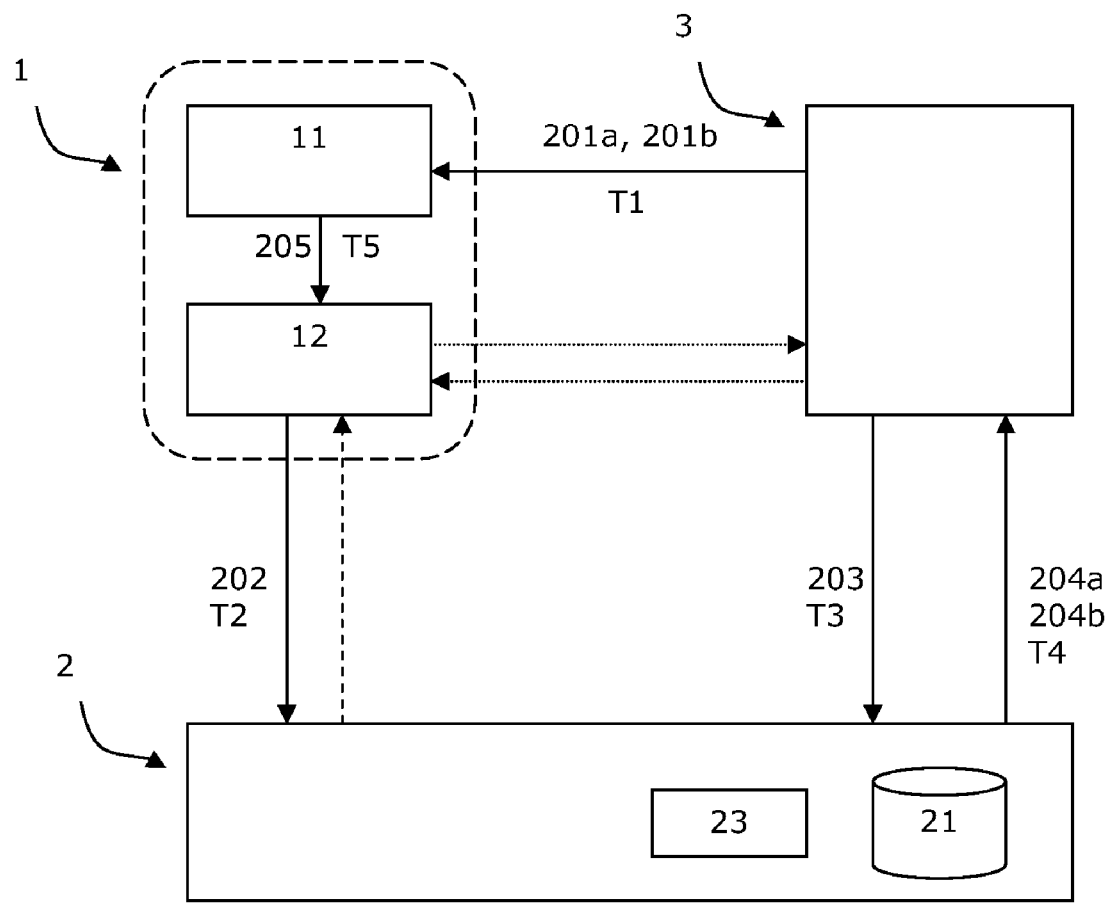
FIG. 2 shows system components and communication procedures during the automatic registration according to a second embodiment variation.

FIG. 2 shows an alternative embodiment of the method and communication sequence of the automatic registration. The basic functionality of the particular system components, patient-bound medical device 1, remote data processing system 2, and programming device 3 are essentially identical, also and in particular in regard to the running operation during the transmission of signal data of the monitored patients, but also for Holter data and statistical storage data having information, for example, about the course of the treatment between aftercare procedures, occurring episodes or technical function parameters, as well as operating procedures and elements described in the following.

If, in this embodiment variation, the method for automatic registration is triggered by the physician on the programming device 3 by actuating a button or a check box, such an operator element, which is only to appear, for optimum support of the physician, when the implant has not yet been registered, in contrast to the embodiment variation shown in FIG. 1, physician identification data 201*a* in the form of an alphanumeric physician key and a registration command 201*b* are first transmitted here in communication step T1 to the implant 11. The transmission of physician identification data 201*a* and registration command 201*b* may occur chronologically independently of one another, or the physician identification data may be transmitted together with the registration command in the scope of a program transmission of the programming device 3 to the implant 11, so that the implant 11 is caused to generate and transmit a registration message 205 directly after ending the programming procedure in communication step T1. After transmitting the registration command 201*b* in the scope of communication step T1, the programming device 3 displays an instruction message on the display screen, that the patient device 12 is to be turned on and it is to be ensured that no further patient device is within the transmission range of the implant 11.

In way not shown in greater detail, the registration command 201*b* received by the implant 11 is executed in that the physician identification data is combined with the device identification data (the serial number of the implant) stored in the implant 11 and the serial number of the patient device 12, which was previously queried from this device via a bidirectional, local wireless connection, to form a data structure and/or a data container.

In this case, the data container may be brought into a specific form so that it may be uniquely recognized as a registration message. Prefixing a header having an assigned identifier suggests itself for this purpose.

The registration message 205 thus resulting is transmitted in communication step T5 to the patient device 12. The patient device in turn transmits the registration message via a mobile wireless connection in communication step T2 to the data processing system 2.

Alternatively, it is possible that initially a registration message 205 is generated in the implant 11, which initially solely has the device identification data of implant 11 and the device identification data of the patient device 12 is first incorporated after communication step T5 in the patient device 12, before the registration message 202 is relayed to the data processing center in communication step T2. This variation may also be implemented if the connection between implant 11 and patient device is a unidirectional connection from implant to patient device.

Simultaneously or after the transmission and/or program transmission in communication step T1, a registration request 203 is generated in the programming device 3, which contains the same alphanumeric short key 201a as the physician identification data, as was transmitted previously in step T1 to the implant 11. This registration request 203 also contains personal information on the physician and on the patient, as well as the device identification data of the patient-bound medical device 1 (at least that of the implant 11) as well as for the user data having a technical and/or administrative intended purpose. It is transmitted assembled into a data container as a registration request and identified as such similarly as the registration message in communication step T3, in parallel to the registration message transmitted via the mobile wireless connection, via a high-performance and sufficiently secure online connection (e.g., Internet via https) to the data processing system 2. After receiving the registration request, the data processing system 2 expects the registration message corresponding to the registration request within a predetermined time window, e.g., three minutes. Accordingly, if the registration message arrives first, the time window may also be triggered by the registration message, so that the registration request matching the registration message is expected within the time window. Recognizing a registration request or message as belonging to the particular other message is performed on the basis of the particular device identification data contained in the messages.

If precisely one registration request and precisely one matching registration message arrive in the data processing system 2 within the predetermined time window, whose beginning and duration are established by the timer 23, the physician identification data contained in the registration message and the device identification data are checked for correspondence with the physician identification and device identification data contained in the associated registration request. If these data correspond, after any further checking of various technical or administrative conditions, such as the comparison of the serial numbers or the physician identification key with information contained in data bank 21 (such as compatibility information between implant 11 and patient device 12, list of certified physicians), the registration of the patient-bound medical device 1 for the physician, whose physician identification data was transmitted, and the patient device, which has transmitted the registration message, is performed. The device identification data of implant 11 and patient device 12 to be stored in the course of the registration in the data bank 21 is taken from the registration message.

In case of successful registration, in communication step T4 a registration confirmation 204a is transmitted via the online connection between programming device 3 and data processing device 2 and a notification window is displayed for the user in programming device 3, which contains the following information: implant type and device identification data (serial number) of the implant registered immediately previously, physician identification data (physician key) and name of the physician, type and identification data of the patient device; in this way, the physician may check the information again for the sake of security and confirm the procedure on his part by actuating an OK button as a control element. However, if no or multiple registration messages arrive for one registration request within the specified time window, in such a way that the identification data contained matches with one another, an error message 204b is correspondingly transmitted to the programming device 3 by the data processing system 2 in communication step T4, upon which a corresponding error message is displayed in the programming device 3, which contains the causes of the failed registration, instructions for correcting the problem, and the request to repeat the registration.

For the deregistration procedure according to this embodiment variation, a deregistration request is transmitted by the programming device 3 via the online connection to the data processing system 2, this deregistration request being triggered by the physician actuating an operating element on the user interface of the programming device.

What is claimed is:

1. A method for automatic registration of a patient-bound medical device (1) at a remote data processing system (2), comprising:
   transmitting physician identification data (102, 201) to a patient-bound medical device (1);
   assembling device identification data from identification data of individual system components (11, 12) of the patient-bound medical device (1);
   combining the physician identification data together with device identification data to form a registration message (103, 205, 202);
   transmitting the registration message (103, 205, 202) by the patient-bound medical device (1) to the data processing system (2); and,
   checking via the data processing system (2), data contained in the registration message (103, 202) and performing a registration in case of success.

2. The method according to claim 1, further comprising checking compatibility of the individual system components (11, 12) via the data processing system (2) using the device identification data.

3. The method according to claim 1, further comprising checking authorization using the physician identification data in the data processing system (2).

4. The method according to claim 1, further comprising:
   querying the device identification data (101) via a programming device (3) from the patient-bound medical device (1, 11);
   combining said device identification data (101) with said physician identification data stored in the programming device (3) to form said registration message (102); and,
   transmitting said registration message (102) via the programming device (3) to the patient-bound medical device (1, 12).

5. The method according to claim 4, further comprising incorporating personal data in the physician identification data.

6. The method according to claim 4, further comprising transmitting a confirmation (104a) via the data processing system (2) to the patient-bound medical device (1, 12) in the case of successful registration and otherwise transmitting an error message (104b).

7. The method according to claim 1, further comprising:
   selecting a key expression (201a) as the physician identification data; and,
   transmitting said physician identification data by a programming device (3) to the patient-bound medical device (1, 11).

8. The method according to claim 7, further comprising transmitting a triggering command (201b) for triggering a registration message from the programming device (3) to the patient-bound medical device (1) and combining the physician identification data with the device identification data stored in the patient-bound medical device to form the registration message in the patient-bound medical device (1).

9. The method according to claim 7, further comprising transmitting a registration request (203) by the programming device (3) to the data processing system (2).

10. The method according to claim 9, further comprising incorporating any combination of the device identification data,
the physician identification data,
personal data
in the registration request (203).

11. The method according to claim 9, further comprising transmitting via the data processing system (2) a confirmation (204*a*) to the programming device (3) in case of successful registration and otherwise transmitting an error message (204*b*).

12. The method according to claim 9, further comprising comparing the data contained in the registration message in the data processing system (2) to the data contained in the registration request.

13. The method according to claim 9, further comprising checking in the data processing system (2) whether registration message (202) and associated registration request (203) have been received within a predefined time slot.

14. The method according to claim 9, further comprising checking in the data processing system (2) whether precisely one registration message (202) has been received for a received registration request (203).

15. The method according to claim 4, further comprising producing an infrared connection between the programming device (3) and the patient-bound medical device (1, 12).

16. The method according to claim 4, further comprising producing an Internet connection between the programming device (3) and the data processing system (2).

17. The method according to claim 1, further comprising producing a movable wireless connection between the patient-bound medical device (1, 12) and the data processing system (2).

18. A programming device (3) configured to program a patient-bound medical device (1) wherein said programming device comprises at least one interface configured to transmit and receive data and having a memory configured to store and retrieve data, a user data input, wherein programming device is further implemented to query device identification data from the patient-bound medical device (1), wherein the programming device is implemented to generate a data structure from the device identification data and the user data and is also implemented to serialize and transmit the data structure as a registration message (102) to the patient-bound medical device (1, 12) wherein the data structure has a first data field configured to store the device identification data of a first system component (11) of the patient-bound medical device (1) and a second data field configured to store the device identification data of a second system component (12) of the patient-bound medical device (1) and further data fields configured to store user data.

19. A programming device (3) configured to program a patient-bound medical device (1) wherein said programming device comprises at least one interface configured to transmit and receive data and having a memory configured to store and retrieve data, a user data input and wherein programming device is further implemented to query querying device identification data from the patient-bound medical device (1), wherein the programming device is also implemented to generate a data structure from the device identification data and the user data, is implemented to serialize and transmit the data structure as a registration request (203) to a data processing system (2), and is also implemented to generate and transmit a triggering command (201) for a registration message to the patient-bound medical device (1, 11) wherein the data structure has a first data field configured to store the device identification data of a first system component (11) of the patient-bound medical device (1) and a second data field configured to store the device identification data of a second system component (12) of the patient-bound medical device (1) and further data fields configured to store user data.

20. A patient-bound medical device (1) having at least one interface configured to transmit and receive data and having stored device identification data and configured to transmit a registration message (103, 202) to a data processing system (2) wherein said patient-bound medical device is further configured to receive and process physician identification data (201*a*) and to receive and process a triggering command (201*b*) for said registration message from a programming device (3) and wherein said patient-bound medical device is further configured to generate a data structure from the device identification data and the physician identification data and further configured to serialize and transmit the data structure as the registration message (205, 202) to the data processing system (2) wherein the data structure has a first data field configured to store the device identification data of a first system component (11) of the patient-bound medical device (1) and a second data field configured to store the device identification data of a second system component (12) of the patient-bound medical device (1) and further data fields configured to store user data.

21. A data processing system (2) having at least one communication interface configured to receive and transmit messages (103, 104*a*, 104*b*, 202, 203, 204*a*, 204*b*) and a memory (21) configured to store and retrieve data, wherein said data processing system is configured to receive a registration message (103, 202) from a patient-bound medical device (1) to check the data contained therein, and to register and to transmit a confirmation message (104*a*, 204*a*) or an error message (104*b*, 204*b*) to said patient-bound medical device (1, 12) or to a programming device (3) or to said patient-bound medical device (1, 12) and said programming device (3) and further comprising a timer (23) to establish a device time frame and wherein said data processing system is configured to check whether precisely one registration message (202) was received within a time frame for a registration request (203).

22. The data processing system according to claim 21, configured to receive the registration request (203) and, furthermore, to bring together registration request (203) so received with a received registration message (202).

23. A configuration for executing the method for automatic registration of a patient-bound medical device at a remote data processing system according to claim 1, having a programming device (3), a patient-bound medical device (1) and a data processing system (2) wherein said programming device is
configured to program said patient-bound medical device (1) wherein said programming device comprises at least one interface configured to transmit and receive data and having a memory configured to store and retrieve data, a user data input configured to obtain user data, wherein said programming device is further implemented to query device identification data from the patient-bound medical device (1), wherein the programming device is implemented to generate a data structure from the device identification data and the user data and is also implemented to serialize and transmit the data structure as a registration message (102) to the patient-bound medical device (1, 12)
wherein the data structure has a first data field configured to store the device identification data of a first system component (11) of the patient-bound medical device (1) and a second data field configured to store the device identification data of a second system component (12) of the patient-bound medical device (1) and further data fields configured to store user data wherein said patient-bound medical device (1) comprises according to claim 22, at least one interface configured to transmit and receive data and having stored device identification data and configured to transmit said registration message (103, 202) to a data processing system (2) wherein said patient-bound medical device is further configured to receive and process physician identification data (201*a*) and to receive and process a triggering command (201*b*) for said registration message from a programming device (3) and wherein said patient-bound medical device is further configured to generate said data structure from the device identification data and the physician identification data and further configured to serialize and transmit the data structure as the registration message (205, 202) to the data processing system (2); and, wherein said data processing system (2) comprises at least one communication interface configured to receive and transmit messages (103, 104*a*, 104*b*, 202, 203, 204*a*, 204*b*) and a memory (21) configured to store and retrieve data, wherein said data processings system is configured to receive a registration message 103 202) from said patient-bound medical device (1) to check the data contained therein, and to register and to transmit a confirmation message (104*a*, 204*a*) or an error message (104*b*, 204*b*) to said patient-bound medical device (1, 12) or to said programming device (3) or to said patient-bound medical device (1, 12) and said programming device (3) and further comprising a timer (23) to establish a device time frame and wherein said data processing system is configured to check whether precisely one registration message (202) was received within a time frame for a registration request (203).

* * * * *